(12) United States Patent
Casas et al.

(10) Patent No.: US 11,969,586 B2
(45) Date of Patent: Apr. 30, 2024

(54) BLOOD PUMP IMPELLER

(71) Applicant: HeartWare, Inc., Miami Lakes, FL (US)

(72) Inventors: Fernando Casas, Miami Lakes, FL (US); Mustafa Ertan Taskin, Durham, NC (US)

(73) Assignee: HeartWare, Inc., Miami Lakes, FL (US)

( * ) Notice: Subject to any disclaimer, the term of this patent is extended or adjusted under 35 U.S.C. 154(b) by 505 days.

(21) Appl. No.: 17/189,399

(22) Filed: Mar. 2, 2021

(65) Prior Publication Data

US 2022/0280769 A1 Sep. 8, 2022

(51) Int. Cl.
*A61M 60/216* (2021.01)
*A61M 60/178* (2021.01)

(52) U.S. Cl.
CPC ........ *A61M 60/216* (2021.01); *A61M 60/178* (2021.01); *A61M 2205/0266* (2013.01); *A61M 2205/04* (2013.01); *A61M 2205/3368* (2013.01); *A61M 2205/36* (2013.01); *A61M 2205/3606* (2013.01); *A61M 2205/502* (2013.01); *A61M 2205/52* (2013.01); *A61M 2250/00* (2013.01)

(58) Field of Classification Search
CPC ...... A61M 2205/0266; A61M 2205/04; A61M 2205/3368; A61M 2205/36; A61M 2205/3606; A61M 2205/502; A61M 2205/52; A61M 2250/00; A61M 60/178; A61M 60/216; A61M 60/237; A61M 60/242; A61M 60/804; A61M 60/806; A61M 60/808
See application file for complete search history.

(56) References Cited

U.S. PATENT DOCUMENTS

| | | |
|---|---|---|
| 5,092,878 A | 3/1992 | Miyata |
| 6,293,901 B1 | 9/2001 | Prem |
| 7,997,854 B2 | 8/2011 | LaRose et al. |
| 8,007,254 B2 | 8/2011 | LaRose et al. |
| 8,419,609 B2 | 4/2013 | Shambaugh, Jr. et al. |
| 8,512,013 B2 | 8/2013 | LaRose et al. |
| 9,217,442 B2 | 12/2015 | Wiessler et al. |
| 9,561,313 B2 | 2/2017 | Taskin |
| 9,907,891 B2 | 3/2018 | Wiessler et al. |
| 2003/0135086 A1 | 7/2003 | Khaw et al. |
| 2008/0114339 A1 | 5/2008 | McBride et al. |
| 2013/0066139 A1 | 3/2013 | Wiessler et al. |

(Continued)

FOREIGN PATENT DOCUMENTS

| | | |
|---|---|---|
| CN | 215135918 U | 12/2021 |
| WO | 2011076441 A1 | 6/2011 |

OTHER PUBLICATIONS

International Search Report and Written Opinion of International Application No. PCT/US2022/015400, dated May 26, 2022, 5 pp.

(Continued)

*Primary Examiner* — Jon Eric C Morales
(74) *Attorney, Agent, or Firm* — Shumaker & Sieffert, P.A.

(57) ABSTRACT

An implantable blood pump including an impeller, at least a portion of the impeller being composed of a metal alloy that is a solid at normal body temperature and is configured to phase change to a liquid between a predetermined temperature above normal body temperature and about 40 degrees Celsius.

20 Claims, 3 Drawing Sheets

(56) References Cited

U.S. PATENT DOCUMENTS

| | | |
|---|---|---|
| 2016/0045654 A1 | 2/2016 | Connor |
| 2016/0271309 A1 | 9/2016 | Throckmorton et al. |
| 2018/0200421 A1 | 7/2018 | Wiessler et al. |
| 2018/0303989 A1 | 10/2018 | Casas |
| 2020/0146141 A1 | 5/2020 | Thrasher et al. |
| 2020/0146142 A1 | 5/2020 | Thrasher et al. |
| 2021/0213185 A1 | 7/2021 | Schafir et al. |
| 2021/0213186 A1 | 7/2021 | Michelena et al. |
| 2022/0280769 A1* | 9/2022 | Casas .................. A61M 60/216 |

OTHER PUBLICATIONS

Fields, "It's a Bird, It's a Plane: Flow Patterns Around an Oscillating Piezoelectric Fan Blade," Nov. 6, 2017, IEEE Spectrum, 7 pp.

* cited by examiner

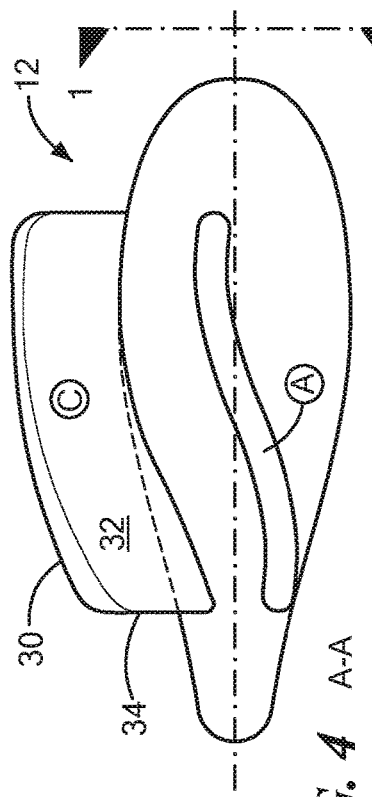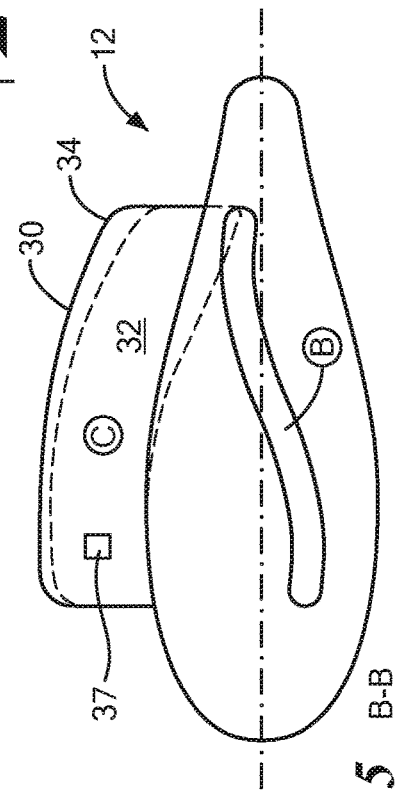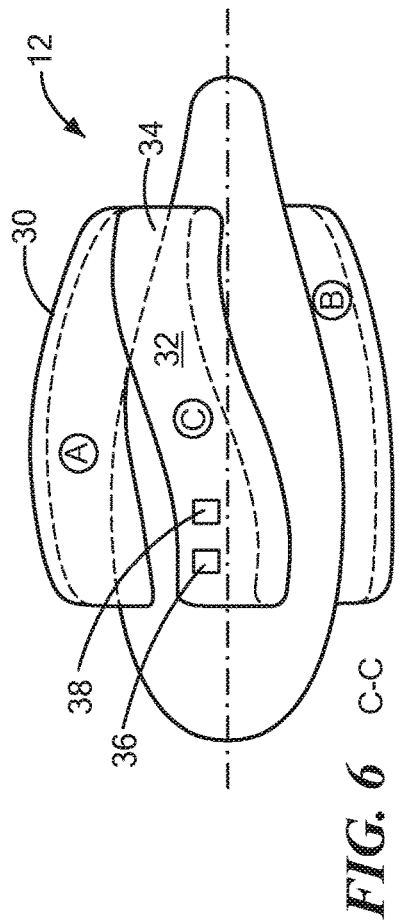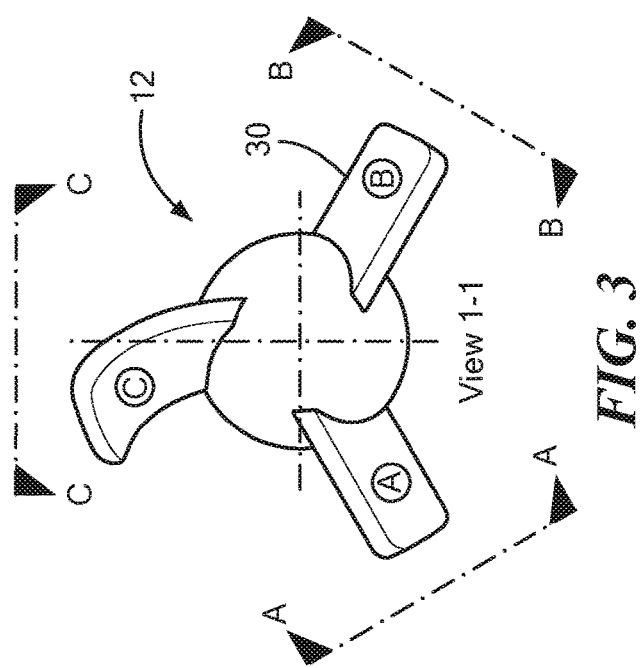

BLOOD PUMP IMPELLER

CROSS-REFERENCE TO RELATED APPLICATION n/a.

FIELD

The present technology is generally related to implantable blood pumps, and in particular, implantable blood pumps with a minimal hemolysis impeller.

BACKGROUND

Implantable blood pumps are commonly used to assist the pumping action of a failing heart and typically include a housing with an inlet, an outlet, and a rotor mounted therein. The inlet may be connected to a chamber of the patient's heart, typically the left ventricle, using an inflow cannula. The outlet may be connected to an artery, such as the aorta. Rotation of the rotor drives blood from the inlet towards the outlet and thus assists blood flow from the chamber of the heart into the artery. A known type of blood pump is a ventricular assist device ("VAD") with examples including, but not limited to, the HVAD® pump and the MVAD® pump manufactured by HeartWare, Inc. in Miami Lakes, Fla., USA.

Current VADs have rotors with a plurality of blades configured to impel blood downstream from the inlet. However, these blades are static in that they have a single shape and profile during the pumping of blood.

SUMMARY

The techniques of this disclosure generally relate to an implantable blood pump impellers.

In one aspect, the present disclosure provides an implantable blood pump including an impeller, at least a portion of the impeller being composed of a metal alloy that is a solid at normal body temperature and is configured to phase change to a liquid between a predetermined temperature above normal body temperature and about 40 degrees Celsius.

In another aspect of this embodiment, the impeller includes a plurality of blades, and wherein the metal alloy is included within at least one of the plurality of blades.

In another aspect of this embodiment, at least one of the plurality of blades includes a flexible material, and wherein the metal alloy is disposed within the flexible material.

In another aspect of this embodiment, the flexible material is a titanium alloy.

In another aspect of this embodiment, the flexible material is a polymer.

In another aspect of this embodiment, during a phase change of the metal alloy to a liquid, the metal alloy causes extension of the flexible material of the at least one of the plurality of blades a distance away from the impeller.

In another aspect of this embodiment, a heating element is coupled to the impeller, wherein the heating element is configured to heat the metal alloy above normal body temperature.

In another aspect of this embodiment, the metal alloy is configured to phase change from a liquid to a solid at about normal body temperature.

In another aspect of this embodiment, a cooling element is coupled to the impeller, wherein the cooling element is configured to cool the metal alloy from temperatures above normal body temperature to normal body temperature.

In another aspect of this embodiment, the pump defines a major longitudinal axis, and wherein the impeller is configured to impel blood along the major longitudinal axis.

In one aspect, an implantable blood pump system includes an impeller, at least a portion of the impeller being composed of a metal alloy that is a solid at normal body temperature and is configured to phase change to a liquid between a predetermined temperature above normal body temperature and about 40 degrees Celsius. A heating element or a cooling element is coupled to the impeller. A controller is in communication with the impeller and with the heating element or the cooling element, the controller being configured to activate the heating element or the cooling element to control a temperature of the metal alloy.

In another aspect of this embodiment, the impeller includes a plurality of blades, and wherein the metal alloy is included within at least one of the plurality of blades.

In another aspect of this embodiment, at least one of the plurality of blades includes a flexible material, and wherein the metal alloy is disposed within the flexible material.

In another aspect of this embodiment, the flexible material is a titanium alloy.

In another aspect of this embodiment, the flexible material is a polymer.

In another aspect of this embodiment, during a phase change of the metal alloy to a liquid, the metal alloy causes extension of the flexible material of the at least one of the plurality of blades a distance away from the impeller.

In another aspect of this embodiment, the pump defines a major longitudinal axis, and wherein the impeller is configured to impel blood along the major longitudinal axis.

In another aspect of this embodiment, a temperature sensor is coupled to the impeller.

In another aspect of this embodiment, the metal alloy is configured to phase change from a liquid to a solid at about normal body temperature.

In one aspect, an impeller included, at least a portion of the impeller comprising a metal alloy that is a solid at normal body temperature and is configured to phase change to a liquid between a predetermined temperature above normal body temperature and about 40 degrees Celsius.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 3 is a top view of an exemplary impeller constructed in accordance with the principles of the present application;

FIG. 4 is a side view of the impeller shown in FIG. 3 across view A-A;

FIG. 5 is a side view of the impeller shown in FIG. 3, across view B-B; and FIG. 6 is a side view of the impeller shown in FIG. 3 across view C-C.

DETAILED DESCRIPTION

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Figure 1:
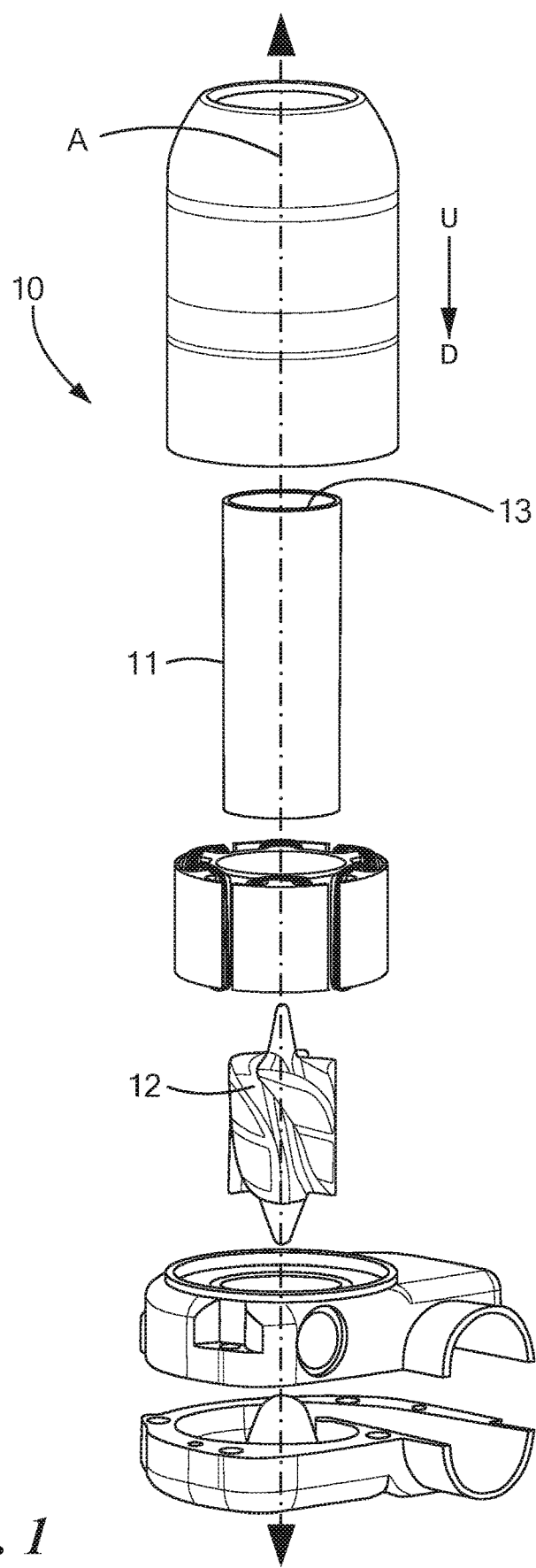
FIG. 1 is a disassembled view of an implantable blood pump.

Referring now to the drawings in which like reference designators refer to like elements there is shown in FIG. 1 a disassembled view of an exemplary implantable blood pump 10 configured to be implanted within a patient, such as a human or animal patient. The blood pump 10 may be, without limitation, the HVAD® pump or the MVAD® pump, having a movable element, such as an impeller 12 or a rotor, configured to rotate about axis "A" and impel blood from the heart to the rest of the body. The impeller 12 may rotate within a tube 11 extending from a proximal upstream end to a distal downstream end. The HVAD® Pump is further discussed in U.S. Pat. Nos. 7,997,854 and 8,512,013, the disclosures of which are incorporated herein by reference in the entirety. The MVAD® Pump is further discussed in U.S. Pat. Nos. 8,007,254, 8,419,609, and 9,561,313, the disclosures of which are incorporated herein by reference in the entirety.

Figure 2:
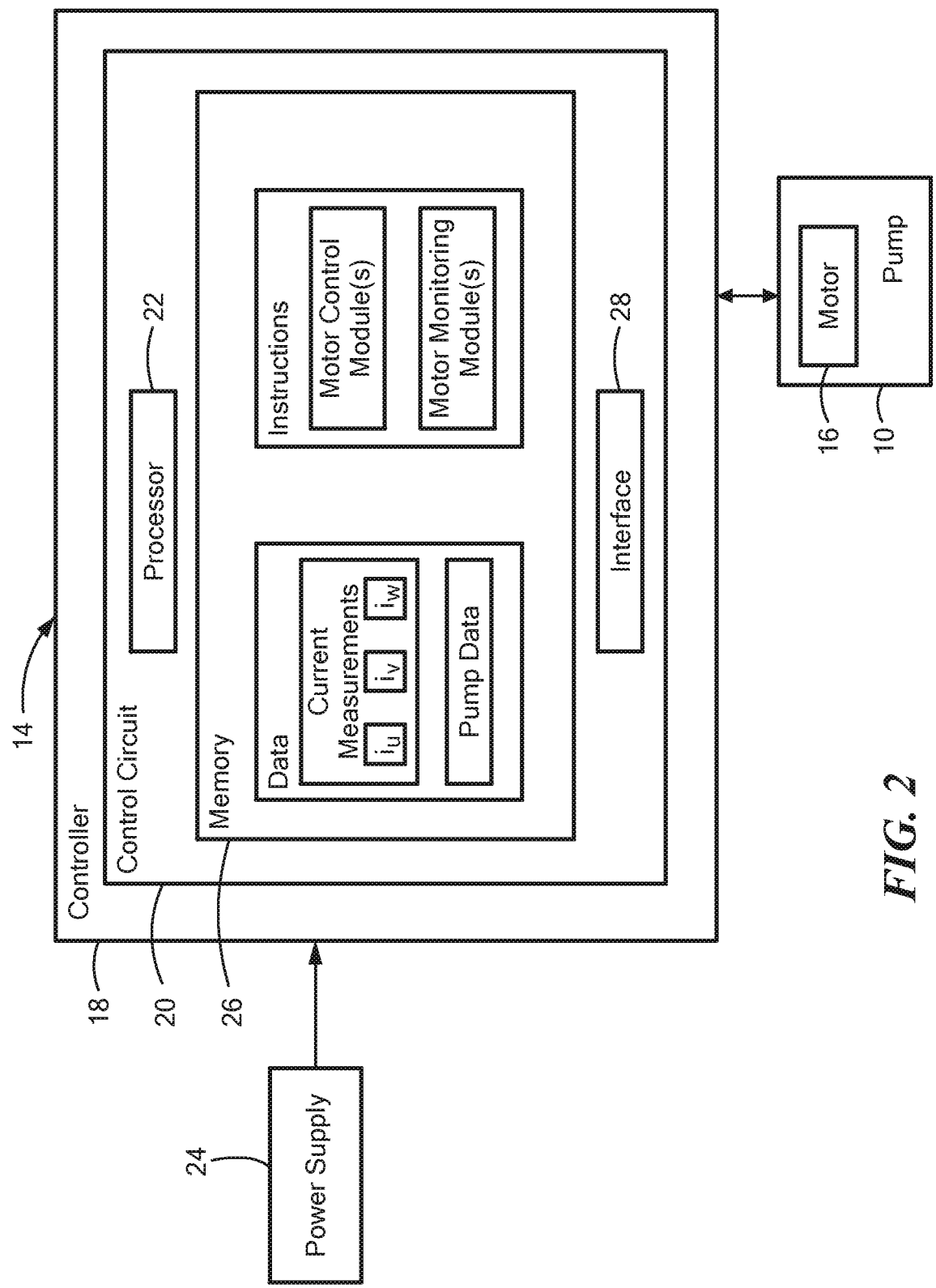
FIG. 2 is a block diagram of a system for controlling a pump speed of the blood pump of FIG. 1.

FIG. 2 is a block diagram of an exemplary system 14 for controlling a pump speed and/or other operations of the implantable blood pump 10 when the blood pump 10 is in communication with the system 14 and powered by a power supply 24. The blood pump 10 includes a motor 16 therein and may be a separate component or form part of the system 14. In one example, the system 14 includes a controller 18 having a control circuit 20 and a processor 22 including processing circuitry configured to perform the operations of the blood pump 10. The system 14 may also include a memory 26 and an interface 28, the memory 26 being configured to store information accessible by the processor 22, including instructions executable by the processing circuitry and/or data that may be retrieved, manipulated or stored by the processor 22. Such instructions and/or data include that which is used to control the pump speed.

Referring now to FIGS. 3-6, the impeller 12 may include a plurality of blades 30 radially disclose about a hub or body 32 of the impeller 12. At least a portion of the impeller 12, for example blade "C", at least one of the plurality of blades 30 may include or otherwise be composed of a metal alloy 32, for example, a Field's metal or gallium, that is a solid at normal body temperature, for example around 37 degrees Celsius and is configured to phase change to a liquid between a predetermined temperature above normal body temperature and about 40 degrees Celsius. In one configuration, at least one of the plurality of blades 30 includes a flexible material 34 that encloses or otherwise houses the metal alloy 32. For example, the flexible material 34 may be Nitinol, a polymer, or a titanium alloy and forms part of the blade 30. For example, the flexible material 34 may form and outer part of the blade 30, like a cover, such that the metal alloy 32 is enclosed within the flexible material 34 and the impeller 12. Thus, when the metal alloy 32 phase changes from a liquid to a solid, and from a solid to a liquid, the flexible material 34 similarly changes shape to accommodate the change in shape of the metal alloy 32. For example, each blade, as shown in FIGS. 3-5 may define a different shape. For example, in an exemplary configuration, the metal alloy 32 is disposed underneath the flexible material 34 in a solid state at normal body temperature and defines a profile for normal operation of the impeller 12. However, at temperatures above normal body temperature, for example, febrile conditions, the metal alloy 32 passively phase changes to a liquid, which similarly changes the shape of the flexible material 34 and the overall profile of the blade 30, which may have the effect of reducing hemolysis about the impeller blade 30. Such a change in shape may function as a rinse of the impeller 12 of thrombus formation and/or prevent hemolysis around the area of the blade 30. For example, the flexible material 34 may define a shape when flexed by the liquid metal alloy 32 that extends the blade out a farther distance away from the hub of the impeller 12 than compared to when the metal alloy 32 is a solid. In other configurations, the flexible material 34 may define channels in which the liquid metal alloy 32 flows. When the temperature is raised a predetermined amount above normal body temperature, the liquid metal alloy 32 flowing within the channels may phase change to solid causing deformation of the flexible material 34.

In one configuration, a heating element 36, such as a resistive heating element may be coupled to or other positioned on or proximate to the metal alloy 32. The heating element 36 maybe in communication with the controller 18, which is configured to modulate the heat generated by the heating element 36 to control the phase change of the metal alloy 32. A temperature sensor 37 may also be included on one of the impeller blades 30 and in further communication with the controller 18. The controller 18 may be configured to modulate the heating element 36 at preset times, for example, every hour on the hour, to cause a phase change of the metal alloy 32. Power for the heating element may supplied by kinetic energy harvesting components as the impeller 12 rotates as disclosed in U.S. patent application Ser. No. 16/952,613, the entirety of which is expressly incorporated by reference herein. Similarly, a cooling element 38, for example a Peltier cooling element, may be coupled or otherwise positioned on or proximate to the metal alloy 32. The cooling element 38 may be powered in a similar manner to that of the heating element 36 and is configured to cool the metal alloy 32 from its liquid state back to its solid state, that is, from temperatures above normal body temperature back to normal body temperature. In one configuration, the controller 18 controls the operation of both the heating element 36 and cooling element 38 by communicating with a wireless transmitter (not shown) on the impeller 12 as part of the kinetic energy harvesting components. In other configurations, the metal alloy 32 may be disposed within the inflow cannula of the pump 10. For example, in a first configuration the inflow cannula may include the metal alloy 32 in a solid configuration, and then when heated, the inflow cannula contracts the lumen within the inflow cannula to prevent retrograde flow. Details about the contraction of the inflow cannula may be found in U.S. patent application Ser. No. 17/100,319, the entirety of which is expressly incorporated by reference herein.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. An implantable blood pump, comprising:
an impeller, at least a portion of the impeller being composed of a metal alloy that is a solid at normal body temperature and is configured to phase change to a liquid between a predetermined temperature above normal body temperature and about 40 degrees Celsius.

2. The pump of claim 1, wherein the impeller includes a plurality of blades, and wherein the metal alloy is included within at least one of the plurality of blades.

3. The pump of claim 2, wherein at least one of the plurality of blades includes a flexible material, and wherein the metal alloy is disposed within the flexible material.

4. The pump of claim 3, wherein the flexible material is a titanium alloy.

5. The pump of claim 3, wherein the flexible material is a polymer.

6. The pump of claim 3, wherein during a phase change of the metal alloy to a liquid, the metal alloy causes extension of the flexible material of the at least one of the plurality of blades a distance away from the impeller.

7. The pump of claim 1, further including a heating element coupled to the impeller, wherein the heating element is configured to heat the metal alloy above normal body temperature.

8. The pump of claim 1, wherein the metal alloy is configured to phase change from a liquid to a solid at about normal body temperature.

9. The pump of claim 1, further including a cooling element coupled to the impeller, wherein the cooling element is configured to cool the metal alloy from temperatures above normal body temperature to normal body temperature.

10. The pump of claim 1, wherein the pump defines a major longitudinal axis, and wherein the impeller is configured to impel blood along the major longitudinal axis.

11. An implantable blood pump system, comprising:
an impeller, at least a portion of the impeller being composed of a metal alloy that is a solid at normal body temperature and is configured to phase change to a liquid between a predetermined temperature above normal body temperature and about 40 degrees Celsius;
a heating element or a cooling element coupled to the impeller; and
a controller in communication with the impeller and with the heating element or the cooling element, the controller being configured to activate the heating element or the cooling element to control a temperature of the metal alloy.

12. The system of claim 11, wherein the impeller includes a plurality of blades, and wherein the metal alloy is included within at least one of the plurality of blades.

13. The system of claim 12, wherein at least one of the plurality of blades includes a flexible material, and wherein the metal alloy is disposed within the flexible material.

14. The system of claim 13, wherein the flexible material is a titanium alloy.

15. The system of claim 13, wherein the flexible material is a polymer.

16. The system of claim 13, wherein during a phase change of the metal alloy to a liquid, the metal alloy causes extension of the flexible material of the at least one of the plurality of blades a distance away from the impeller.

17. The system of claim 11, wherein the pump defines a major longitudinal axis, and wherein the impeller is configured to impel blood along the major longitudinal axis.

18. The system of claim 11, further including a temperature sensor coupled to the impeller.

19. The system of claim 11, wherein the metal alloy is configured to phase change from a liquid to a solid at about normal body temperature.

20. An impeller, at least a portion of the impeller comprising a metal alloy that is a solid at normal body temperature and is configured to phase change to a liquid between a predetermined temperature above normal body temperature and about 40 degrees Celsius.

* * * * *